United States Patent
Koizumi et al.

(10) Patent No.: US 11,496,468 B2
(45) Date of Patent: Nov. 8, 2022

(54) ENDOSCOPE SYSTEM, TERMINAL DEVICE, AND CONTROL METHOD

(71) Applicant: OLYMPUS CORPORATION, Tokyo (JP)

(72) Inventors: Yugo Koizumi, Yokohama (JP); Hidekazu Shinano, Tokyo (JP); Hideyuki Kugimiya, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 264 days.

(21) Appl. No.: 16/883,378

(22) Filed: May 26, 2020

(65) Prior Publication Data
US 2020/0287899 A1    Sep. 10, 2020

Related U.S. Application Data

(63) Continuation of application No. PCT/JP2018/038875, filed on Oct. 18, 2018.

(30) Foreign Application Priority Data

Nov. 27, 2017   (JP) .............................. JP2017-227190

(51) Int. Cl.
*H04L 9/32*       (2006.01)
*G06F 21/00*    (2013.01)
(Continued)

(52) U.S. Cl.
CPC ....... *H04L 63/0861* (2013.01); *H04N 5/2253* (2013.01); *H04N 7/183* (2013.01);
(Continued)

(58) Field of Classification Search
CPC .. H04L 63/0861; H04N 5/2253; H04N 7/183; H04N 2005/2255; H04W 12/06; H04W 88/02
(Continued)

(56) References Cited

U.S. PATENT DOCUMENTS

2003/0128400 A1   7/2003  Watai et al.
2006/0174133 A1*  8/2006  Obata ................... G06F 21/31
                                                                    713/182
(Continued)

FOREIGN PATENT DOCUMENTS

CN       207356062 U   *  5/2018
JP       2003-164413 A      6/2003
(Continued)

OTHER PUBLICATIONS

Jan. 8, 2019 Search Report issued in International Patent Application No. PCT/JP2018/038875.

*Primary Examiner* — Haresh N Patel
(74) *Attorney, Agent, or Firm* — Oliff PLC

(57) ABSTRACT

An endoscope system includes a processor that performs image processing on endoscope image data acquired by an endoscope, which is inserted in a subject and observes an inside of the subject. The processor communicate with a terminal device including a transceiver configured to transmit identification information identifying the terminal device, and a controller configured to: determine whether the processor is a connection destination configured to perform two-way communication, based on the received processor identification information, authenticate whether a user of the terminal device is a predetermined registered user by analyzing data obtained by the terminal device from the user, and allow two-way communication between the processor and the terminal device in response to the processor being determined as the connection designation to perform two-way communication and in response to authenticating the user of the terminal device.

21 Claims, 7 Drawing Sheets

(51) Int. Cl.
*H04L 9/40* (2022.01)
*H04N 5/225* (2006.01)
*H04N 7/18* (2006.01)
*H04W 12/06* (2021.01)
*G06F 7/04* (2006.01)
*H04W 88/02* (2009.01)

(52) U.S. Cl.
CPC .... *H04W 12/06* (2013.01); *H04N 2005/2255* (2013.01); *H04W 88/02* (2013.01)

(58) Field of Classification Search
USPC .............................................................. 726/7
See application file for complete search history.

(56) References Cited

U.S. PATENT DOCUMENTS

| | | | |
|---|---|---|---|
| 2009/0268018 A1* | 10/2009 | Kasai | A61B 1/0004 348/E7.085 |
| 2011/0034769 A1* | 2/2011 | Adair | A61B 1/00032 600/110 |
| 2013/0241693 A1* | 9/2013 | Miyamoto | H04W 12/06 340/5.6 |
| 2017/0302874 A1* | 10/2017 | Adair | A61B 1/00135 |

FOREIGN PATENT DOCUMENTS

| | | |
|---|---|---|
| JP | 2009-213790 A | 9/2009 |
| JP | 2013-244044 A | 12/2013 |
| JP | 2017-117295 A | 6/2017 |

* cited by examiner

ENDOSCOPE SYSTEM, TERMINAL DEVICE, AND CONTROL METHOD

CROSS-REFERENCE TO RELATED APPLICATION

This application is a continuation of PCT International Application No. PCT/JP2018/038875 filed on Oct. 18, 2018, which designates the United States, incorporated herein by reference, and which claims the benefit of priority from Japanese Patent Application No. 2017-227190, filed on Nov. 27, 2017, incorporated herein by reference.

BACKGROUND

1. Technical Field

The present disclosure relates to an endoscope system that displays image data which is obtained by inserting an endoscope into a subject and imaging an inside of a body of the subject, and relates to a terminal device, and a control method.

2. Related Art

In the related art, in systems for supporting endoscope inspection tasks, technology is known that supports inspection-related tasks and cleaning-related tasks by setting respective inspection schedules and cleaning schedules for an endoscope and notifying medical workers including doctors of these schedules (see JP 2017-117295 A). With this technology, a schedule for endoscope inspection tasks is suitably implemented as a result of receiving a confirmation notification from a medical worker after reporting activity content with notification timing that has been decided on the basis of a time designated by planned inspection start time information included in the inspection schedule, and activity content performed by the medical worker before the start of the inspection.

SUMMARY

In some embodiments, an endoscope system includes a processor configured to perform image processing on endoscope image data acquired by an endoscope, which is inserted in a subject and observes an inside of the subject; and a terminal device communicating with the processor, the terminal device including: a transceiver configured to transmit identification information identifying the terminal device to the processor and receive, from the processor, processor identification information identifying the processor, and a controller configured to: determine whether the processor is a connection destination configured to perform two-way communication, based on the received processor identification information, authenticate whether a user of the terminal device is a predetermined registered user by analyzing data obtained by the terminal device from the user, and allow two-way communication between the processor and the terminal device in response to the processor being determined as the connection designation to perform two-way communication and in response to authenticating the user of the terminal device.

In some embodiments, provided is a terminal device is configured to communicate with a processor that performs image processing on endoscope image data acquired by an endoscope that observes an inside of a subject. The terminal device includes a transceiver configured to transmit identification information identifying the terminal device to the processor and receive, from the processor, authentication information allowing two-way communication; and a controller communicating with the transceiver, the controller being configured to: determine whether the processor is a connection destination configured to perform two-way communication, based on the received processor identification information, authenticate whether a user of the terminal device is a predetermined registered user by analyzing data obtained by the terminal device from the user, and allow two-way communication between the processor and the terminal device in response to the processor being determined as the connection designation to perform two-way communication and in response to authenticating the user of the terminal device.

In some embodiments, provided is a control method executed by an endoscope system including (i) a processor configured to perform image processing on endoscope image data acquired by an endoscope, which is inserted in a subject and observes an inside of the subject, the processor being configured to connect to a network, and (ii) a terminal device configured to communicate wirelessly with the processor or the network. The control method includes transmitting identification information identifying the terminal device to the processor; receiving, from the processor, authentication information allowing wireless two-way communication; determining, based on the authentication information, whether the processor is a connection destination configured to perform wireless two-way communication; authenticating whether a user of the terminal device is a predetermined registered user by analyzing data obtained by the terminal device from the user; and allowing wireless two-way communication between the processor and the terminal device, or wireless two-way communication between the network and the terminal device in response to the processor being determined as the connection designation to perform two-way communication and in response to authenticating the user of the terminal device.

The above and other features, advantages and technical and industrial significance of these embodiments will be better understood by reading the following detailed description of presently preferred embodiments of the disclosure, when considered in connection with the accompanying drawings.

DETAILED DESCRIPTION

As a mode for carrying out the disclosure (hereinafter called "embodiment"), an endoscope system including an endoscope that images a body cavity of a subject, such as a patient, and that displays images will be described hereinbelow by way of example. In addition, the disclosure is not limited to or by the following embodiment. Furthermore, the same reference signs are assigned to the same parts in the disclosures of the drawings.

Endoscope System Configuration

Figure 1:
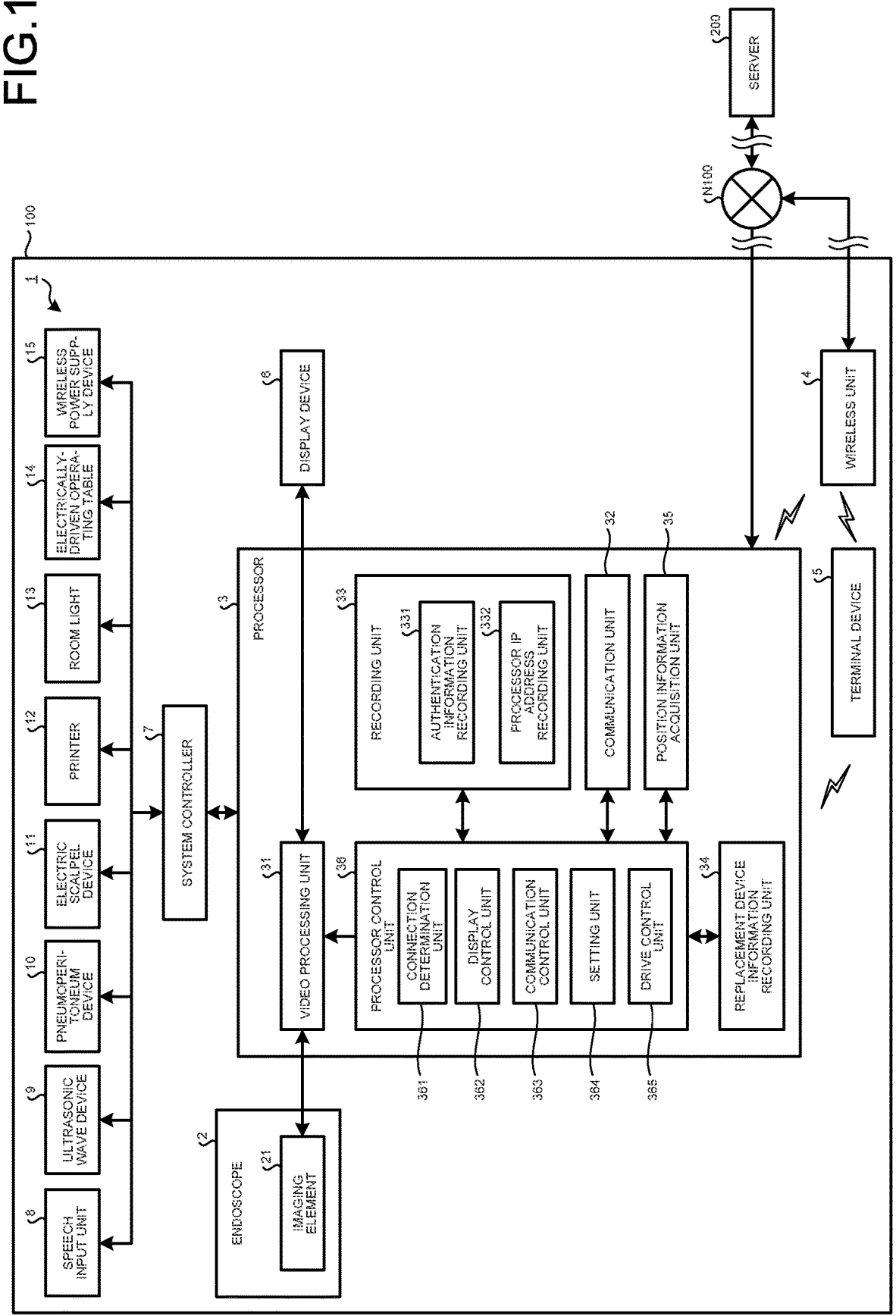
FIG. 1 is a block diagram illustrating a function configuration of an endoscope system according to one embodiment of the disclosure.

FIG. 1 is a block diagram illustrating a function configuration of an endoscope system according to one embodiment of the disclosure. An endoscope system 1 illustrated in FIG. 1 is used when medical workers, including at least doctors, perform an endoscope surgical operation, an endoscope inspection, or an endoscope treatment on a subject such as a patient, in an operating room 100 in a hospital. The endoscope system 1 includes an endoscope 2, a processor 3, a wireless unit 4, a terminal device 5, a display device 6, a system controller 7, a speech input unit 8, an ultrasonic wave device 9, a pneumoperitoneum device 10, an electric scalpel device 11, a printer 12, a room light 13, an electrically-driven operating table 14, and a wireless power supply device 15.

First, the configuration of the endoscope 2 will be described. The endoscope 2 is inserted into a subject. The endoscope 2 is configured using a rigid endoscope or a flexible endoscope. Based on control by the processor 3, the endoscope 2 irradiates the inside of a subject with illumination light, generates endoscope image data by imaging an area of the inside of the subject which has been irradiated with the illumination light, and outputs the generated endoscope image data to the processor 3. The endoscope 2 includes an imaging element 21 that generates image data by imaging the inside of the subject. The imaging element 21 is configured using an image sensor such as a charge coupled device (CCD) or a complementary metal oxide semiconductor (CMOS), or using an A/D conversion circuit, or the like. Note that the endoscope 2 is connected to the processor 3 by a cable or wirelessly so as to be capable of bidirectional communication. In addition, when the endoscope image data generated by the endoscope 2 is transmitted wirelessly, the endoscope image data may be sequentially transmitted to the processor 3 via the wireless unit 4, described subsequently, or the endoscope image data may be sequentially transmitted via a network N100 to a server 200 which is installed in the hospital and outside the operating room 100.

Next, the configuration of the processor 3 will be described. The processor 3 controls the endoscope 2, performs predetermined image processing on endoscope image data which is sequentially input from the endoscope 2, and makes sequential outputs to the display device 6. The processor 3 includes a video processing unit 31, a communication unit 32, a recording unit 33, a replacement device information recording unit 34, and a processor control unit 36.

The video processing unit 31 performs predetermined image processing on the endoscope image data which is input from the endoscope 2 and makes outputs to the display device 6. Here, the predetermined image processing is synchronization processing, demosaicing processing (when the imaging element 21 is a Bayer array), white balance adjustment processing, γ-correction processing, saturation adjustment processing, and format conversion processing, or the like. The video processing unit 31 is configured using a field programmable gate array (FPGA), an application specific integrated circuit (ASIC) and a graphics processing unit (GPU), or the like.

The communication unit 32 is configured using a communication module and performs bidirectional communication with the terminal device 5 according to a predetermined communication standard. Furthermore, the communication unit 32 performs bidirectional communication with the terminal device 5 via the wireless unit 4 or with the server 200, which is installed in the hospital, via the network N100. Here, the predetermined communication standard is wireless fidelity (Wi-Fi) (registered trademark) communication, Bluetooth (registered trademark) communication, and Bluetooth Low Energy (registered trademark) communication (hereinafter simply called "BLE communication"), or the like. For example, in the case of Wi-Fi, a local network is assumed, and where device roles are concerned, there is a relationship between access points and stations and, where the overall connection processing is concerned, the relationship is such that stations are connected to the wireless network whereon the access points are constructed. As an approximate connection sequence, the wireless unit 4, which is an access point, first constructs a wireless network and reports its own network identifier (SSID). Thereafter, the communication unit 32 of the processor 3, which is a station, searches for the reported network identifier (SSID) and connects to the desired network (access point). Because a network of multiple devices is assumed, the coverage is broad, and strict identification steps are followed while considering the problem of interference. Hence, it sometimes takes time to establish a connection. However, data communication enables data to be sent and received with the timing of the respective access points and stations. Note that the communication unit 32 may adopt communication using 4G wireless in addition to Wi-Fi communication. Obviously, the communication unit 32 could also adopt other communication such as communication using 3G wireless, communication using 5G wireless, worldwide interoperability for microwave access (WiMAX) (registered trademark) communication, and infrared communication (infrared data association (IrDA) (registered trademark)) or the like.

The recording unit 33 records various programs which are executed by the processor 3, data undergoing processing and endoscope image data, and the like. The recording unit 33 is configured using a flash memory, a synchronous dynamic random access memory (SDRAM), a memory card, or a solid state drive (SSD), or the like. Furthermore, the recording unit 33 includes an authentication information recording unit 331 that records device addresses and connectivity determination information of devices for which wireless two-way communication has been authenticated; and a processor IP address recording unit 332 that records processor identification information including a processor IP address identifying the processor 3.

The replacement device information recording unit 34 transmits replacement periods for each of the devices constituting the processor 3 wirelessly to the devices located within a predetermined range. The replacement device information recording unit 34 is configured using wireless tags, for example, radio frequency identifiers (RFIDs).

A position information acquisition unit 35 acquires position information issued by the terminal device 5. The position information acquisition unit 35 is configured using an RFID reader or a communication module which is capable of Bluetooth communication, for example.

The processor control unit 36 controls various devices constituting the endoscope system 1 and the respective parts of the processor 3. The processor control unit 36 is configured using a central processing unit (CPU) or the like. The processor control unit 36 includes a connection determination unit 361, a display control unit 362, a communication control unit 363, a setting unit 364, and a drive control unit 365.

The connection determination unit 361 determines, on the basis of a terminal IP address and an authentication result which are transmitted from the terminal device 5, whether or not the terminal device 5 is a connection destination which is capable of wireless two-way communication.

The display control unit 362 controls display modes of the display device 6. Specifically, the display control unit 362 causes the display device 6 to display endoscope images which correspond to endoscope image data that has undergone image processing by the video processing unit 31. Furthermore, if wireless two-way communication between the processor 3 and the terminal device 5 has been established, the display control unit 362 causes the display device 6 to display information to the effect that the processor 3 and the terminal device 5 are capable of wireless two-way communication.

The communication control unit 363 allows communication between the terminal device 5 and a plurality of peripheral devices on the basis of the determination result of the connection determination unit 361 and the authentication result which has been transmitted from the terminal device 5.

The setting unit 364 sets a plurality of peripheral devices which the terminal device 5 is capable of operating via the system controller 7 on the basis of a level assigned to a registered user in the authentication result transmitted from the terminal device 5.

The drive control unit 365 controls the driving of the peripheral devices by controlling the system controller 7 on the basis of a request signal and an operating signal which are input from the terminal device 5 via the communication unit 32.

Next, the configuration of the wireless unit 4 will be described. The wireless unit 4 is connected to the server 200 via the network N100 and is connected to the processor 3 and the terminal device 5 so as to be capable of bidirectional communication according to a predetermined communication standard. The wireless unit 4 adopts Wi-Fi communication. Furthermore, the wireless unit 4 is installed in the periphery of the processor 3 or on a wall surface or the like in the operating room 100.

Next, the configuration of the terminal device 5 will be described. The terminal device 5 communicates bidirectionally with the processor 3 according to a predetermined communication standard and receives and displays endoscope image data generated by the endoscope 2 and case image data from the server 200 via the wireless unit 4. In addition, the terminal device 5 acquires at least one of a software program and setting information from the processor 3 or from the server 200 which is connected to the network N100, the software program being a program of the respective devices constituting the endoscope system 1, the setting information being information for the respective devices constituting the endoscope system 1 which has been set by a registered user who is able to use the terminal device 5. Furthermore, the terminal device 5 receives inputs of operating signals and request signals for manipulating the operations of the respective devices constituting the endoscope system 1 via the processor 3 or the wireless unit 4. Note that the detailed configuration of the terminal device 5 will be described subsequently.

Next, the configuration of the display device 6 will be described. On the basis of control by the display control unit 362, the display device 6 displays images which correspond to image data which is input from the video processing unit 31 and various information of the endoscope system 1. The display device 6 is configured using a liquid-crystal or organic electroluminescence (EL) display monitor and a loudspeaker or the like that outputs speech to the outside.

The system controller 7 is connected to the processor 3 by a cable or wirelessly, and individually controls the speech input unit 8, the ultrasonic wave device 9, the pneumoperitoneum device 10, the electric scalpel device 11, the printer 12, the room light 13, the electrically-driven operating table 14, and the wireless power supply device 15 according to instruction signals which are input from the processor 3. When referring to any one of the speech input unit 8, the ultrasonic wave device 9, the pneumoperitoneum device 10, the electric scalpel device 11, the printer 12, the room light 13, the electrically-driven operating table 14, and the wireless power supply device 15 hereinbelow, same will simply be called a "peripheral device". Furthermore, the system controller 7 is connected to each peripheral device by a cable or wirelessly. The system controller 7 is configured using a CPU and a flash memory, or the like.

On the basis of control by the system controller 7, the speech input unit 8 collects speech emitted by a sound source or a speaker and converts the speech to an analog speech signal (an electrical signal), performs A/D conversion processing and gain adjustment processing on this speech signal to generate digital speech data, and outputs same to the processor 3 via the system controller 7. The speech input unit 8 is configured using any one microphone among a unidirectional microphone, a nondirectional microphone, and a bidirectional microphone, and an A/D conversion circuit and a signal processing circuit, or the like.

The ultrasonic wave device 9 is connected to the endoscope 2 and, on the basis of control by the system controller 7, sends and receives ultrasonic waves via an ultrasound transducer which is provided at the distal end of the endoscope 2. In addition, the ultrasonic wave device 9 outputs ultrasound image data to the system controller 7 on the basis of ultrasonic waves which are received via the endoscope 2. Note that the ultrasonic wave device 9 may generate ultrasound image data of a subject via a dedicated ultrasonic probe.

On the basis of control by the system controller 7, the pneumoperitoneum device 10 emits pneumoperitoneum gas, for example, carbon dioxide, into the subject.

On the basis of control by the system controller 7, the electric scalpel device 11 drives an electric scalpel by applying a predetermined voltage to the electric scalpel.

On the basis of control by the system controller 7, the printer 12 outputs an image that corresponds to image data which has been input from the processor 3.

The room light 13 is provided in a plurality in the operating room 100, and on the basis of control by the system controller 7, projects light onto the subject and the operating room 100 using a predetermined illuminance. The room light 13 is configured using a light emitting diode (LED) lamp and a dimmer switch, or the like.

For the electrically-driven operating table 14, a subject is disposed on an operating table. On the basis of control by the system controller 7, the electrically-driven operating table 14 changes the position and posture of the subject by moving the operating table in a vertical direction and a horizontal direction. The electrically-driven operating table 14 is configured using an operating table that is capable of moving in a vertical direction and a horizontal direction and a drive unit such as a motor for driving the operating table.

On the basis of control by the system controller 7, the wireless power supply device 15 supplies power wirelessly to the terminal device 5. The wireless power supply device 15 is configured using any one of an electromagnetic induction system, a magnetic field resonance system, an electrolytic binding system, and a radio wave transmission/reception system.

The server 200 is installed in the hospital and outside the operating room 100, and records, in association with patient IDs (patient information) identifying patients, endoscope image data which is transmitted from the processor 3 or the terminal device 5 via the network N100. Furthermore, upon receiving an image request signal requesting case image data and endoscope image data via the network N100 or the wireless unit 4, the server 200 transmits the case image data and the endoscope image data to the processor 3 or the terminal device 5 which issued the image request signal. Note that, here, endoscope image data includes moving image data and still image data (captured image data).

Terminal Device Configuration

Figure 2:
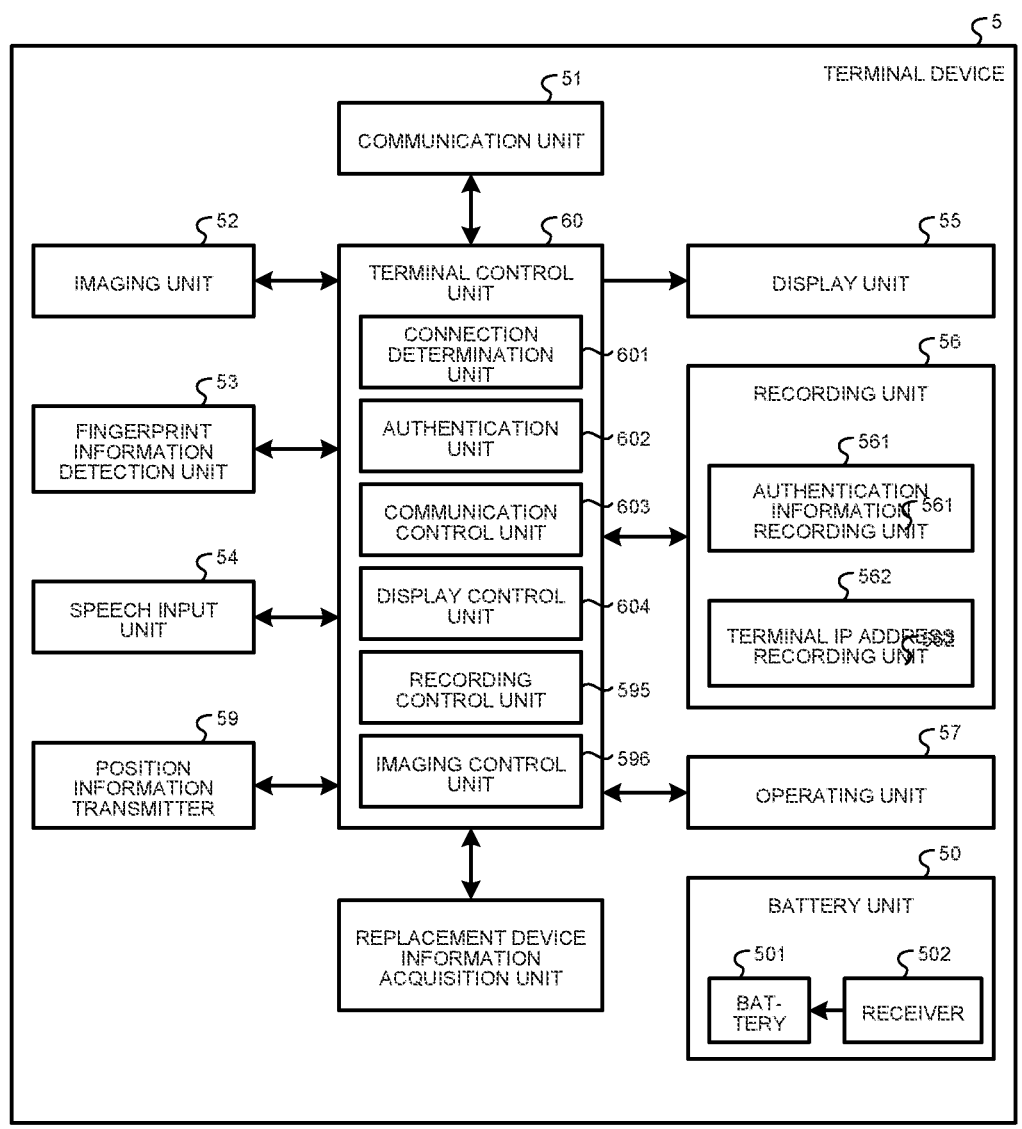
FIG. 2 is a block diagram illustrating a function configuration of a terminal device according to the embodiment of the disclosure.

Next, the detailed configuration of the terminal device 5 described in FIG. 1 will be described. FIG. 2 is a block diagram illustrating a function configuration of the terminal device 5.

The terminal device 5 illustrated in FIG. 2 includes a battery unit 50, a communication unit 51, an imaging unit 52, a fingerprint information detection unit 53, a speech input unit 54, a display unit 55, a recording unit 56, an operating unit 57, a replacement device information acquisition unit 58, a position information transmitter 59, and a terminal control unit 60.

The battery unit 50 includes a battery 501 that supplies power to the respective parts constituting the terminal device 5, and a receiver 502 that receives the electromagnetic waves supplied from the wireless power supply device 15, converts same to a current, and supplies the current to the battery 501.

The communication unit 51 is configured using a communication module and performs bidirectional communication with the processor 3 according to a predetermined communication standard. Furthermore, the communication unit 51 performs bidirectional communication with the server 200 via the wireless unit 4 and the in-hospital network N100. Here, Wi-Fi communication is assumed as the predetermined communication standard. Note that the communication unit 51 may adopt communication using 4G wireless in addition to Wi-Fi communication. Obviously, the communication unit 51 could also adopt other communication such as Bluetooth communication, BLE communication, communication using 3G wireless, communication using 5G wireless, WiMAX communication, and infrared communication, or the like.

On the basis of control by the terminal control unit 60, the imaging unit 52 generates image data by imaging the user of the terminal device 5, and outputs the image data to the terminal control unit 60. The imaging unit 52 is configured using an image processing engine or the like which is realized by using an image sensor such as a CCD or a CMOS, A/D conversion processing, and an FPGA or a GPU, or the like. Note that, by providing the imaging unit 52 with an infrared lamp capable of projecting infrared light and an image sensor provided with pixels capable of imaging the infrared light projected by the infrared lamp, the surface irregularities of a user's face may be acquired.

The fingerprint information detection unit 53 detects fingerprint information from the finger of a user as a result of being touched from outside and outputs the detection results to the terminal control unit 60. The fingerprint information detection unit 53 is configured using a fingerprint sensor. Note that the fingerprint information detection unit 53 could also be of the sliding type, for example, in addition to the push-type. Naturally, the fingerprint information detection unit 53 may also detect user veins in addition to fingerprints.

On the basis of control by the terminal control unit 60, the speech input unit 54 collects speech emitted by a sound source or a narrator and converts the speech to an analog speech signal (an electrical signal), performs A/D conversion processing and gain adjustment processing on this speech signal to generate digital speech data, and outputs same to the terminal control unit 60. The speech input unit 54 is configured using any one microphone among a unidirectional microphone, a nondirectional microphone, and a bidirectional microphone, and an A/D conversion circuit and a signal processing circuit, or the like.

The display unit 55 displays image data and various information which are input from the terminal control unit 60. The display unit 55 is configured using a display panel such as a liquid-crystal or organic-EL display panel.

The recording unit 56 records various programs executed by the terminal device 5, data undergoing processing, and image data, and the like. The recording unit 56 is configured using a flash memory, an SSD, and a memory card, or the like. Furthermore, the recording unit 56 includes an authentication information recording unit 561, and a terminal IP address recording unit 562 that records a terminal IP address identifying the terminal device 5.

The operating unit 57 receives inputs of instruction signals corresponding to operations from the user. The operating unit 57 is configured using a touch panel, buttons, and switches, or the like.

The replacement device information acquisition unit 58 acquires wireless transmissions which are transmitted from the replacement device information recording unit 34 provided in the processor 3 and makes outputs to the terminal control unit 60. The replacement device information acquisition unit 58 is configured using an RFID reader.

The position information transmitter 59 transmits position information relating to the position of the terminal device 5 up to a predetermined distance. Specifically, the position information transmitter 59 transmits position information up to a reachable distance within the operating room 100. The position information transmitter 59 is configured using a communication module that is capable of RFID or Bluetooth communication, for example.

The terminal control unit 60 integrally controls the respective parts constituting the terminal device 5. The terminal control unit 60 is configured using a CPU or the like. The terminal control unit 60 includes a connection determination unit 601, an authentication unit 602, a communication control unit 603, a display control unit 604, a recording control unit 605, and an imaging control unit 606.

The connection determination unit 601 determines, on the basis of authentication information which the communication unit 51 receives from the processor 3, whether or not the processor 3 is a connection destination capable of wireless two-way communication.

The authentication unit 602 authenticates whether or not the user of the terminal device 5 is a registered user who has been registered beforehand. Specifically, the authentication unit 602 performs authentication in which any one or more of a facial image of the user of the terminal device 5, biological information of the user, and gesture information of the user are acquired. For example, the authentication unit 602 determines whether or not features of a facial image of a user who appears in an image corresponding to the image data generated by the imaging unit 52 match the features of the face of a registered user recorded by the recording unit 56.

The communication control unit 603 allows wireless two-way communication between the processor 3 and the terminal device 5 or wireless two-way communication between the network N100 and the terminal device 5 on the basis of the determination result of the connection determination unit 601 and the authentication result of the authentication unit 602.

The display control unit 604 controls the display modes of the display unit 55. Specifically, the display control unit 604 causes the display unit 55 to display an endoscope image corresponding to the endoscope image data and a case image corresponding to the case image data so as to enable a comparison of these images.

The recording control unit 605 causes the recording unit 56 to record a patient rounds time period which is included in schedule information acquired by the communication control unit 603 in association with endoscope image data.

In cases where a user is authenticated by the authentication unit 602 as being a registered user, the imaging control unit 606 activates the imaging function of the imaging unit 52 by the user of the terminal device 5.

Terminal Device Processing

Figure 3:
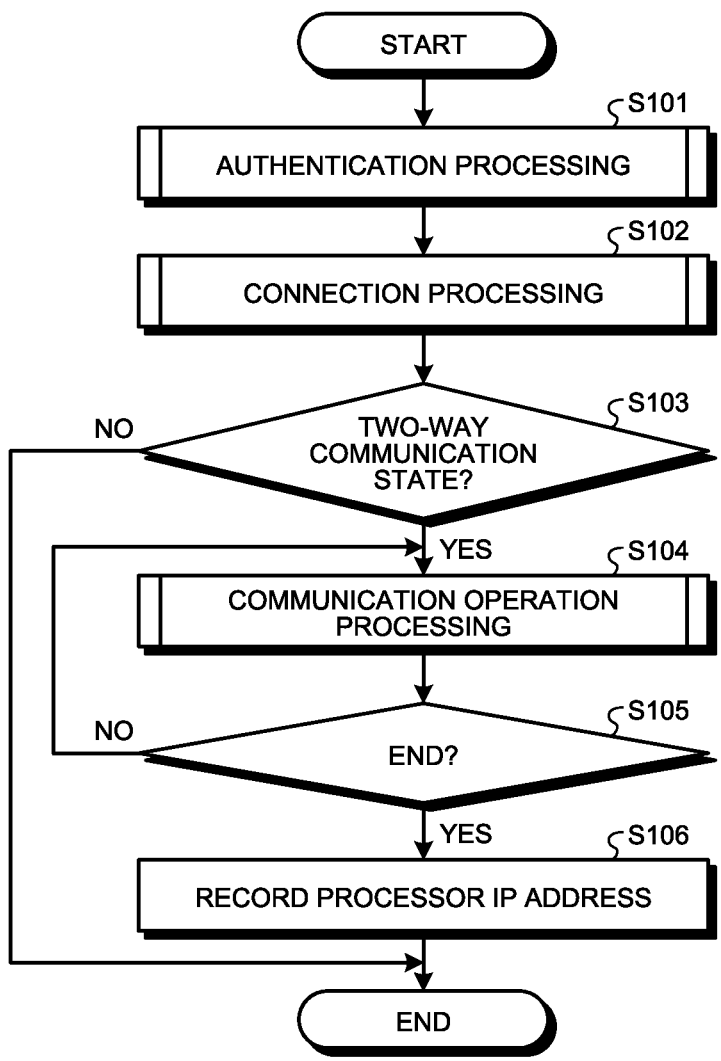
FIG. 3 is a flowchart illustrating an overview of processing executed by a terminal device 5.

The processing executed by the terminal device 5 will be described next. FIG. 3 is a flowchart illustrating an overview of processing executed by the terminal device 5.

As illustrated in FIG. 3, the terminal device 5 first executes authentication processing that performs authentication of whether or not the user of the terminal device 5 is a registered user who is able to operate the terminal device 5 (step S101). After step S101, the terminal device 5 moves to step S102, described subsequently.

Authentication Processing

Figure 4:
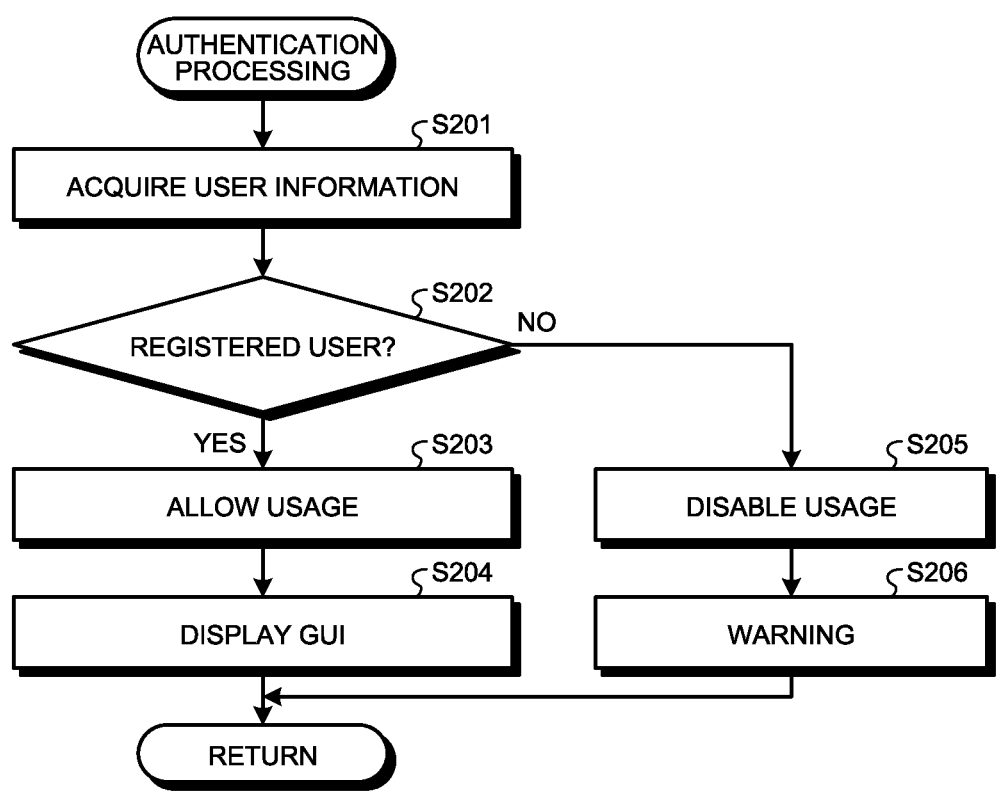
FIG. 4 is a flowchart illustrating details of the authentication processing of FIG. 3.

Next, the details of the authentication processing described in step S101 of FIG. 3 will be described. FIG. 4 is a flowchart illustrating the details of the authentication processing.

As illustrated in FIG. 4, the authentication unit 602 acquires user information of the terminal device 5 (step S201). Specifically, the authentication unit 602 acquires, from any one of the imaging unit 52, the fingerprint information detection unit 53, and the speech input unit 54, image data obtained by the imaging unit 52 imaging the user of the terminal device 5, fingerprint information for the user as detected by the fingerprint information detection unit 53, and speech data generated by the speech input unit 54, respectively.

Thereafter, the authentication unit 602 determines whether or not the user is a registered user on the basis of the user information of the terminal device 5 and the authentication information recorded by the authentication information recording unit 561 (step S202). Specifically, the authentication unit 602 authenticates whether or not the user is a registered user on the basis of the image data generated by the imaging unit 52 and the authentication information recorded by the authentication information recording unit 561. More specifically, the authentication unit 602 determines whether or not there is a predetermined match rate between the feature points of the face of a user appearing in the image corresponding to the image data generated by the imaging unit 52, and the feature points of the face of a registered user included in the authentication information recorded by the authentication information recording unit 561, and authenticates the user as being a registered user when there is a predetermined match rate, and authenticates the user as not being a registered user when there is not a predetermined match rate. Furthermore, the authentication unit 602 authenticates whether or not the user is a registered user on the basis of the fingerprint information detected by the fingerprint information detection unit 53 and the authentication information recorded by the authentication information recording unit 561. More specifically, the authentication unit 602 determines whether or not there is a predetermined match rate between the feature points of user fingerprint information detected by the fingerprint information detection unit 53, and the feature points of registered-user fingerprint information included in the authentication information recorded by the authentication information recording unit 561, and authenticates the user as being a registered user when there is a predetermined match rate, and authenticates the user as not being a registered user when there is not a predetermined match rate. In addition, the authentication unit 602 authenticates whether or not the user is a registered user on the basis of the speech data generated by the speech input unit 54 and the authentication information recorded by the authentication information recording unit 561. More specifically, the authentication unit 602 determines whether or not there is a predetermined match rate between the feature points of the voice print of the speech data generated by the speech input unit 54, and the feature points of the voice print of a registered user included in the authentication information recorded by the authentication information recording unit 561, and authenticates the user as being a registered user when there is a predetermined match rate, and authenticates the user as not being a registered user when there is not a predetermined match rate. In addition, the authentication unit 602 determines whether or not there is a predetermined match rate between gesture information of a user appearing in the image corresponding to the image data generated by the imaging unit 52, and the gesture information included in the authentication information recorded by the authentication information recording unit 561, and authenticates the user as being a registered user when there is a predetermined match rate, and authenticates the user as not being a registered user when there is not a predetermined match rate. Here, gesture information is the number of times the user blinks, the shape of their mouth, their face and hand actions, and the like, for example. When it is determined by the authentication unit 602 that the user of the terminal device 5 is a registered user (step S202: Yes), the authentication unit 602 allows the user to use the terminal device 5 (step S203).

Thereafter, the display control unit 604 causes the display unit 55 to display a GUI or the like which is capable of receiving user operation inputs (step S204). Note that, although the display control unit 604 causes the display unit 55 to display a GUI or the like which is capable of receiving user operation inputs, the fact that usage of the terminal device 5 is allowed may be reported using a loudspeaker or the like (not illustrated). That is, the display control unit 604 functions as a reporting unit that reports the fact that wireless two-way communication between the processor 3 and the terminal device 5 or wireless two-way communication between the network N100 and the terminal device 5 is possible. After step S204, the terminal device 5 returns to the foregoing main routine of FIG. 3.

When the authentication unit 602 determines in step S202 that the user of the terminal device 5 is not a registered user (step S202: No), the authentication unit 602 disables usage of the terminal device 5 by the user (step S205).

Thereafter, the display control unit 604 disables the display unit 55 or causes the display unit 55 to display a warning (step S206). Note that, although the display control unit 604 disables the display unit 55 or causes the display unit 55 to display a warning, the display control unit 604 may output a warning via a loudspeaker or the like (not illustrated). After step S206, the terminal device 5 returns to the foregoing main routine of FIG. 3.

Returning to FIG. 3, the description of step S102 and subsequent steps will now be resumed.

In step S102, the terminal device 5 executes connection processing to establish a connection with the processor 3 for bidirectional communication therewith (step S102). After step S102, the terminal device 5 moves to step S103, described subsequently.

Connection Processing

Figure 5:
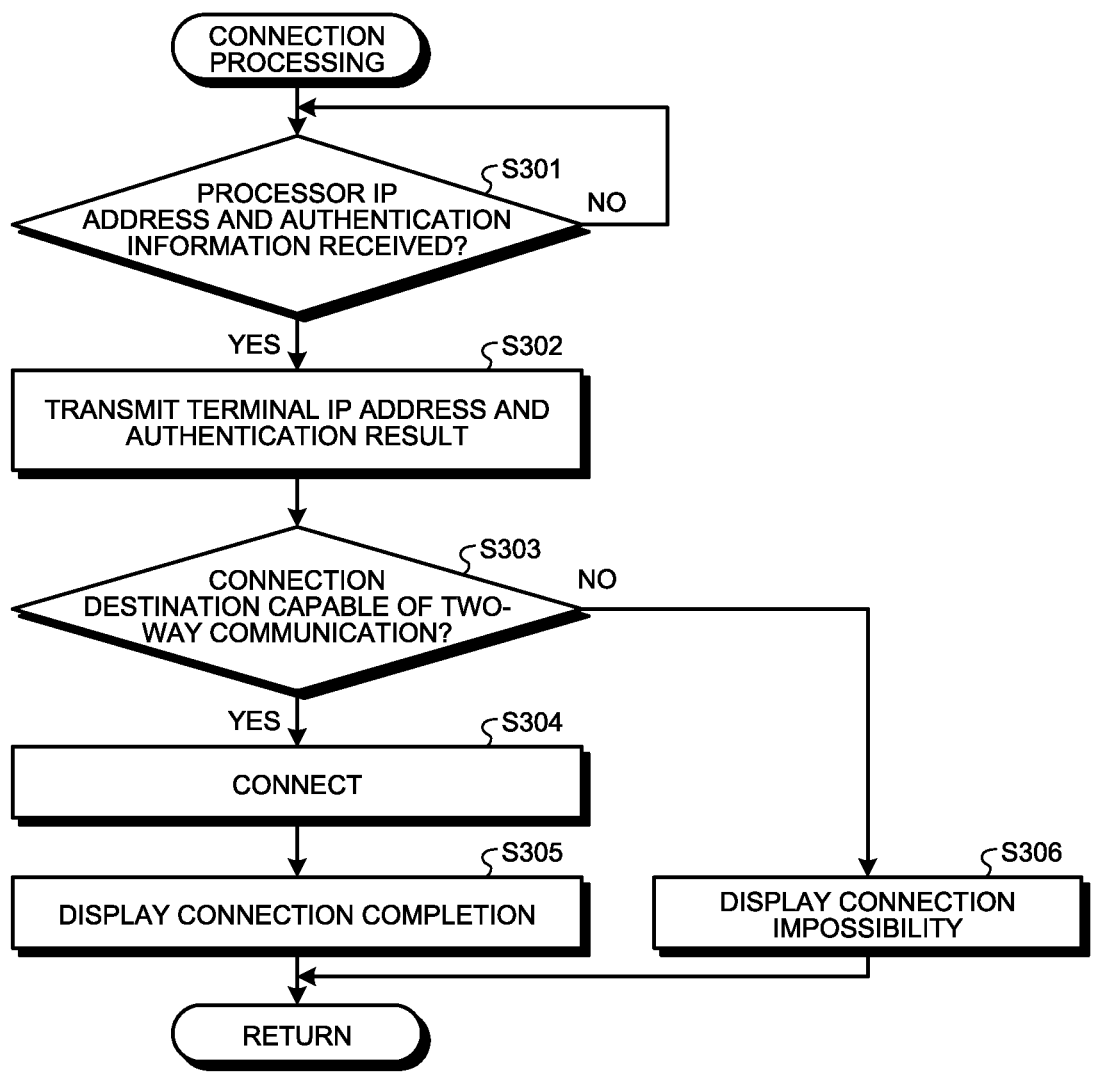
FIG. 5 is a flowchart illustrating details of the connection processing of FIG. 3.

Next, the details of the connecting processing described in step S102 of FIG. 3 will be described. FIG. 5 is a flowchart illustrating the details of the connecting processing.

As illustrated in FIG. 5, the connection determination unit 601 first determines whether or not a processor IP address (SSID) and authentication information have been received from the processor 3 via the communication unit 51 (step S301). Here, authentication information is information for requesting an authentication result of the authentication unit 602 which functions as a password for performing wireless two-way communication with the processor 3. When it is determined by the connection determination unit 601 that a processor IP address and authentication information have been received from the processor 3 via the communication unit 51 (step S301: Yes), the terminal device 5 moves to step S302, described subsequently. In contrast, when it is determined by the connection determination unit 601 that a processor IP address and authentication information have not been received from the processor 3 via the communication unit 51 (step S301: No), the terminal device 5 performs this determination at predetermined time intervals (every ten seconds, for example).

Thereafter, the communication control unit 603 causes the communication unit 51 to transmit, to the processor 3, the terminal IP address recorded in the terminal IP address recording unit 562 by the recording unit 56 and the authentication result authenticated by the authentication unit 602 (step S302). In this case, the communication control unit 603 causes the communication unit 51 to transmit the terminal IP address and the authentication result to the access point (the SSID of the processor 3 or the SSID of the wireless unit 4) which the user has pre-selected via the operating unit 57. Note that, although the access point is the processor 3 or the wireless unit 4 in the present embodiment, the terminal device 5 may also be used as the access point. In this case, the communication control unit 603 may transmit, via the communication unit 51, a terminal IP address (SSID) indicating that the terminal device 5 lies within a predetermined range, for example, a Wi-Fi communication range.

In step S303, the connection determination unit 601 determines whether or not the processor IP address received by the communication unit 51 is a connection destination capable of two-way communication with the terminal device 5 (step S303). Specifically, the connection determination unit 601 determines whether or not the processor IP address is the processor IP address (SSID) which the user has selected via the operating unit 57. When it is determined by the connection determination unit 601 that the processor IP address received by the communication unit 51 is a connection destination capable of two-way communication with the terminal device 5 (step S303: Yes), the terminal device 5 moves to step S304, described subsequently. In contrast, when it is determined by the connection determination unit 601 that the processor IP address received by the communication unit 51 is not a connection destination capable of two-way communication with the terminal device 5 (step S303: No), the terminal device 5 moves to step S306, described subsequently.

In step S304, the communication control unit 603 connects the terminal device 5 to the processor 3 so as to enable two-way communication therebetween. Thus, the terminal device 5 assumes a state of being capable of two-way communication with the processor 3.

Thereafter, the display control unit 604 causes the display unit 55 to display a connection completion indicating that the connection with the processor 3 is complete (step S305). Thus, the user is able to intuitively grasp that a state enabling two-way communication with the processor 3 has been assumed. After step S305, the terminal device 5 returns to the main routine of FIG. 3. Note that, although the display control unit 604 causes connection completion to be displayed by the display unit 55, the disclosure is not limited to such a feature, rather, the fact that a connection with the processor 3 is complete may also be output by a loudspeaker (not illustrated) or may be reported by driving a vibrating section (not illustrated) such as a motor, for example.

In step S306, the display control unit 604 causes the display unit 55 to display a connection impossibility to the effect that a connection with the processor 3 is not possible. Thus, the user is able to intuitively grasp that a connection with the processor 3 is not possible. After step S306, the terminal device 5 returns to the main routine of FIG. 3.

Returning to FIG. 3, the description of step S103 and subsequent steps will now be resumed.

When the terminal device 5 and the processor 3 assume a two-way communication state in step S103 (step S103: Yes), the terminal device 5 executes communication operation processing to control the respective parts of the endoscope system 1 by communicating with the processor 3 in response to operations for which inputs are received by the operating unit 57 (step S104). After step S104, the terminal device 5 moves to step S105. In contrast, when the terminal device 5 and the processor 3 do not assume a two-way communication state (step S103: No), the terminal device 5 ends this processing.

Communication Operation Processing

Figure 6A:
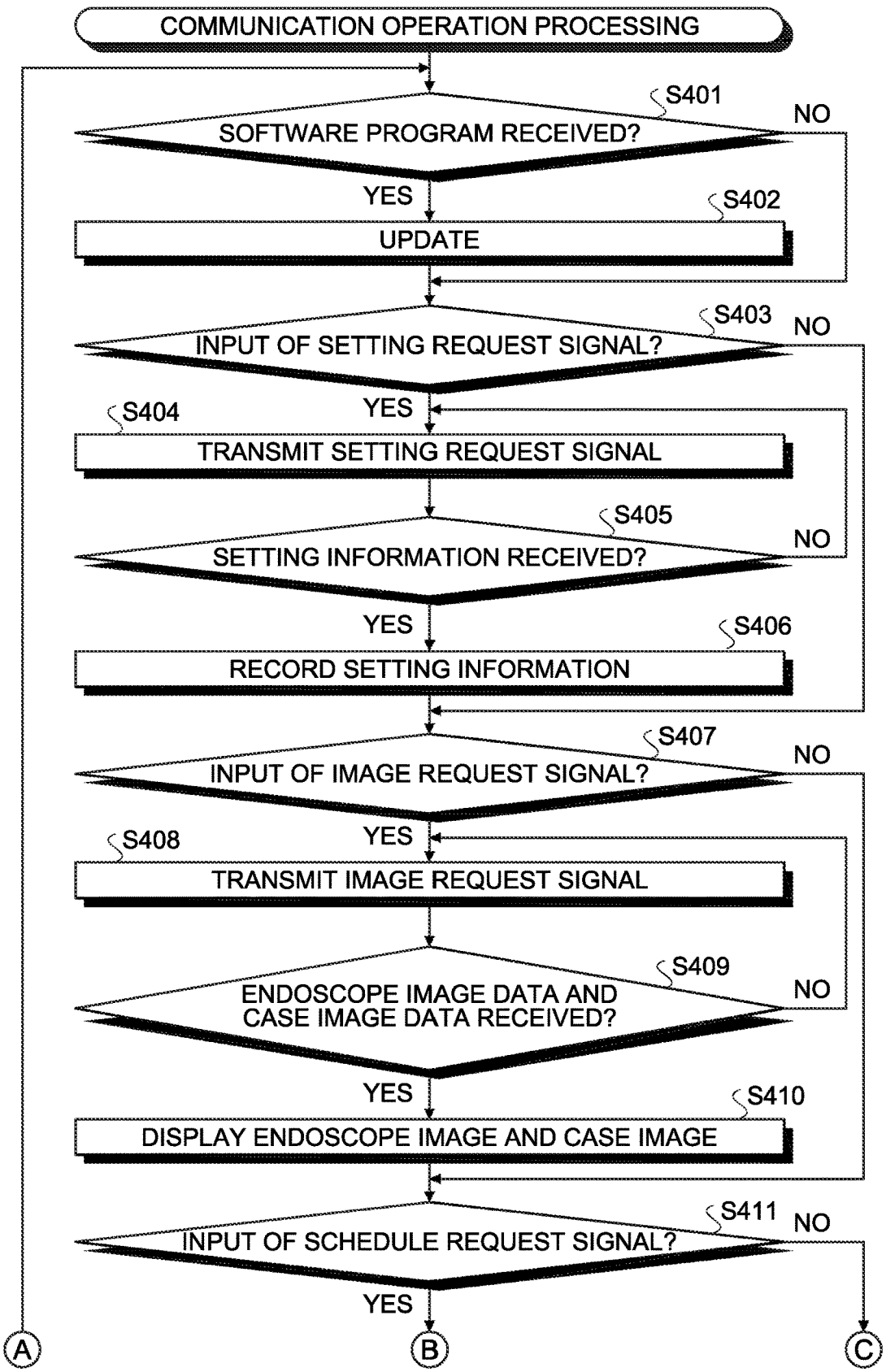
FIGS. 6A-6B show a flowchart illustrating details of the communication operation processing of FIG. 3.
Figure 6B:
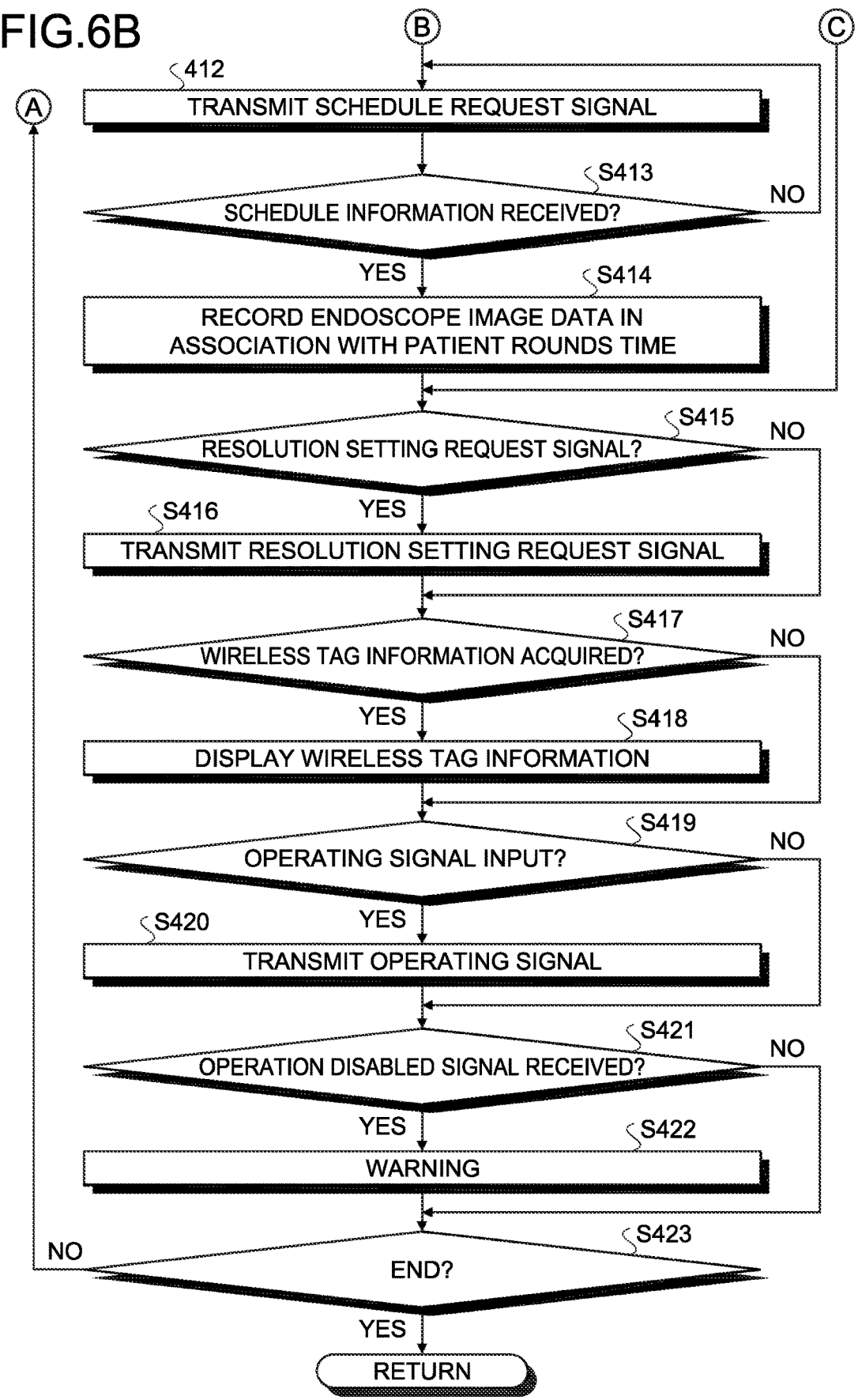

Next, the details of the communication operation processing in step S104 of FIG. 3 above will be described. FIGS. 6A-6B show a flowchart illustrating details of the communication operation processing.

As illustrated in FIGS. 6A-6B, first, when a software program has been received from the processor 3 via the communication unit 51 (step S401: Yes), the terminal control unit 60 updates the software program recorded in the recording unit 56 (step S402). Thus, the terminal device 5 is capable of updating the program for operating the peripheral devices and the processor 3 to the latest program. Furthermore, the software program includes parameters for setting the initial values of the peripheral devices as well as updating the program of the peripheral devices and the processor 3. After step S402, the terminal device 5 moves to step S403, described subsequently. In contrast, when a software program has not been received from the processor 3 via the communication unit 51 (step S401: No), the terminal device 5 moves to step S403, described subsequently.

When an input of a setting request signal requesting setting information has been made from the operating unit 57 in step S403 (step S403: Yes), the communication control unit 603 causes the communication unit 51 to transmit the setting request signal to the processor 3 (step S404). Here, setting information is set parameters which are set by the user from set parameters with initial values for the peripheral devices.

Thereafter, when the communication unit 51 has received setting information from the processor 3 (step S405: Yes), the communication control unit 603 records the setting information in the recording unit 56 (step S406). In this case, the communication control unit 603 may transmit the setting information to the processor 3 via the communication unit 51. The processor 3 is thus capable of automatically setting the set parameters of the peripheral devices to the set parameters which have been set by the user of the terminal device 5 via the system controller 7 on the basis of the setting information. Note that the communication control unit 603 may request the setting information from the server 200 via the communication unit 51 and the wireless unit 4. After step S406, the terminal device 5 moves to step S407, described subsequently. In contrast, when the communication unit 51 has not received setting information from the processor 3 (step S405: No), the terminal device 5 returns to step S404 above.

When an input of a setting request signal requesting setting information has not been made from the operating unit 57 in step S403 (step S403: No), the terminal device 5 moves to step S407, described subsequently.

When, in step S407, an input of an image request signal requesting endoscope image data generated by the endoscope 2 and case image data recorded by the server 200 has been made from the operating unit 57 (step S407: Yes), the communication control unit 603 causes the communication unit 51 to transmit the image request signal to the processor 3 (step S408).

Thereafter, when the communication unit 51 has received endoscope image data and the case image data from the processor 3 (step S409: Yes), the display control unit 604 causes the display unit 55 to display an endoscope image corresponding to the endoscope image data and a case image corresponding to the case image data which have been received by the communication unit 51 (step S410). In this case, when the endoscope image data received by the communication unit 51 is moving image data which is sequentially transmitted, the display control unit 604 sequentially updates, in chronological order, the endoscope image corresponding to the endoscope image data. Furthermore, the display control unit 604 causes the display unit 55 to display the endoscope image and the case image so as to enable a comparison of these images. For example, the display control unit 604 may cause the display unit 55 to display the endoscope image and the case image in parallel, may cause the display unit 55 to display a case image, which has been reduced by a predetermined ratio, by superposing the case image on the endoscope image, or may cause the display unit 55 to display an endoscope image, which has been reduced by a predetermined ratio, by superposing the endoscope image on the case image. After step S410, the terminal device 5 moves to step S411, described subsequently. In contrast, when the communication unit 51 has not received endoscope image data or case image data from the processor 3 (step S409: No), the terminal device 5 returns to step S408 above.

When, in S407, an input of an image request signal requesting endoscope image data generated by the endoscope 2 and case image data recorded by the server 200 has not been made from the operating unit 57 (step S407: No), the terminal device 5 returns to step S411, described subsequently.

When, in step S411, an input of a schedule request signal requesting schedules that include a surgery schedule, a treatment schedule, a rounds schedule, and a hospital discharge schedule, and the like, for a subject, has been made from the operating unit 57 (step S411: Yes), the communication control unit 603 causes the communication unit 51 to transmit the schedule request signal to the processor 3 (step S412).

Thereafter, when the communication unit 51 has received schedule information from the processor 3 (step S413: Yes), the communication control unit 603 records the endoscope image data received in step S410 above in the recording unit 56 in association with a patient rounds time period included in the schedule information (step S414). After step S414, the terminal device 5 moves to step S415, described subsequently. In contrast, when the communication unit 51 has not received schedule information from the processor 3 (step S413: No), the terminal device 5 returns to step S412 above.

When, in step S411, an input of a schedule request signal requesting schedules that include a surgery schedule, a treatment schedule, a rounds schedule, and a hospital discharge schedule, and the like, for a subject, has not been made from the operating unit 57 (step S411: No), the terminal device 5 moves to step S415, described subsequently.

When, in step S415, an input of a resolution setting request signal for setting the resolution of endoscope image data and the resolution of case image data which are received from the processor 3 has been made from the operating unit 57 (step S415: Yes), the communication control unit 603 causes the communication unit 51 to transmit the resolution setting request signal to the processor 3 (step S416). After step S416, the terminal device 5 moves to step S417, described subsequently. In contrast, when an input of a resolution setting request signal for setting the resolution of endoscope image data and the resolution of case image data which are received from the processor 3 has not been made from the operating unit 57 (step S415: No), the terminal device 5 moves to step S417, described subsequently.

When, in step S417, the replacement device information acquisition unit 58 has acquired wireless tag information from the replacement device information recording unit 34 provided in the processor 3 (step S417: Yes), the display control unit 604 causes the display unit 55 to display the wireless tag information (step S418). Thus, a medical worker is able to intuitively grasp a replacement period for replaceable devices in the endoscope system 1. After step S418, the terminal device 5 moves to step S419, described subsequently. In contrast, when the replacement device information acquisition unit 58 has not acquired wireless tag information from the replacement device information recording unit 34 provided in the processor 3 (step S417: No), the terminal device 5 moves to step S419, described subsequently.

When, in step S419, an input of an operating signal for operating peripheral devices has been made from the operating unit 57 (step S419: Yes), the communication control unit 603 transmits the operating signal to the processor 3 via the communication unit 51 (step S420). After step S420, the terminal device 5 moves to step S421, described subsequently. In contrast, when an input of an operating signal for operating peripheral devices has not been made from the operating unit 57 (step S419: No), the terminal device 5 moves to step S421, described subsequently.

When, in step S421, the communication unit 51 has received an operation disabled signal indicating that peripheral devices cannot be operated from the processor 3 (step S421: Yes), the display control unit 604 causes the display unit 55 to display a warning to the effect that operation of the peripheral devices at the user level of the terminal device 5 is prohibited (step S422). After step S422, the terminal device 5 moves to step S423, described subsequently. In contrast, when the communication unit 51 has not received an operation disabled signal indicating that peripheral devices cannot be operated from the processor 3 (step S421: No), the terminal device 5 moves to step S423, described subsequently.

When, in step S423, an instruction signal ending the operation of the endoscope system 1 has been input from the operating unit 57 while performing communication with the processor 3 (step S423: Yes), the terminal device 5 returns to the main routine of FIG. 3. In contrast, when an instruction signal ending the operation of the endoscope system 1 has not been input from the operating unit 57 while performing communication with the processor 3 (step S423: No), the terminal device 5 returns to step S401 above.

Returning to FIG. 3, the description of step S105 and subsequent steps will now be resumed.

When, in step S105, an instruction signal ending the operation by the terminal device 5 has been input from the operating unit 57 (step S105: Yes), the terminal device 5 moves to step S106, described subsequently. In contrast, when an instruction signal ending the operation by the terminal device 5 has not been input from the operating unit 57 (step S105: No), the terminal device 5 returns to step S104 above.

In step S106, the communication control unit 603 records the processor IP address of the processor 3 in the recording unit 56. After step S106, the terminal device 5 ends this processing.

According to the embodiment of the disclosure described hereinabove, the communication control unit 603 allows wireless two-way communication between the processor 3 and the terminal device 5 on the basis of the determination result of the connection determination unit 601 and the authentication result of the authentication unit 602, and hence both efficiency and information security can be taken into account.

In addition, according to the embodiment of the disclosure, when the processor 3 and the terminal device 5 have assumed a state enabling wireless two-way communication, the communication control unit 603 acquires, via the communication unit 51, at least one of a software program and setting information from the processor 3 or from the server 200 which is connected to the network N100, the software program being a program pertaining to the endoscope system 1, the setting information being information relating to various parameters for the peripheral devices constituting the endoscope system 1 which have been set by a registered user, and hence, at all such times, an operation can be performed very quickly by using the terminal device 5 and without setting peripheral device parameters.

Further, according to the embodiment of the disclosure, the display control unit 604 causes the display unit 55 to display an endoscope image corresponding to the endoscope image data and a case image corresponding to the case image data, which have been acquired by the communication control unit 603, so as to enable a comparison of these images, and hence the endoscope image and the case image may be compared while being viewed.

In addition, according to the embodiment of the disclosure, the recording control unit 605 records, in the recording unit 56 in association with endoscope image data, the patient rounds time period included in the schedule information, and hence the user of the terminal device 5 may perform rounds of a patient such as a subject by using endoscope images while performing the rounds.

Furthermore, according to the embodiment of the disclosure, the communication control unit 603 causes the communication unit 51 to transmit a resolution setting request signal for setting, for the processor 3 or the server 200, the resolution of the endoscope image data, and hence the capacity of the endoscope image data can be restricted.

Note that, according to the embodiment of the disclosure, the imaging control unit 606 may activate the imaging function of the imaging unit 52 when the authentication unit 602 has authenticated the user of the terminal device 5 as being a registered user. Information security can accordingly be secured.

In addition, according to the embodiment of the disclosure, when the user of the terminal device 5 has been authenticated as being a registered user by the authentication unit 602, the communication control unit 603 may allow transmission of information to outside the operating room 100 by the communication unit 51. Specifically, the communication control unit 603 may cause information for which an input by the operating unit 57 has been received, such as the findings of a user regarding a subject, for example, to be output by the communication unit 51 to the server 200 outside the operating room 100, or the like. Information security can accordingly be secured.

In addition, according to the embodiment of the disclosure, when the user of the terminal device 5 has been authenticated as being a registered user by the authentication unit 602, the communication control unit 603 may cause the communication unit 51 to transmit information for which an input by the operating unit 57 has been received, such as patient cases or treatment content, for example, to the server 200 which is connected to the network N100. Information security can accordingly be secured.

In addition, according to the embodiment of the disclosure, when the wireless unit 4 has received terminal IP address information from the terminal device 5, the wireless unit 4 may transmit, to the terminal device 5, connectivity determination information indicating whether or not wireless two-way communication with the terminal device 5 is possible. Thus, the operation of the endoscope system 1 using the terminal device 5 can be performed via the wireless unit 4. Here, connectivity determination information is a wireless IP address (SSID) of the wireless unit 4 and a password to allow a connection to the wireless unit 4 at this wireless IP address.

In addition, according to the embodiment of the disclosure, when the wireless unit 4 holds connectivity determination information, the wireless unit 4 may establish an automatic connection between the terminal device 5 and the wireless unit 4 on the basis of the connectivity determination information after the terminal device 5 is powered on. Thus, operability can be improved. Obviously, the terminal device 5 may also establish an automatic connection between the terminal device 5 and the wireless unit 4 on the basis of the connectivity determination information after the terminal device 5 is powered on.

Moreover, according to the embodiment of the disclosure, wireless two-way communication between the server 200, which is connected to the network N100, and the terminal device 5 may be allowed. Accordingly, both efficiency and information security can be taken into account.

Further Embodiments

By suitably combining a plurality of constituent elements which are disclosed in the foregoing embodiment of the disclosure, various inventions can be formed. For example, several constituent elements may be removed from among all the constituent elements disclosed in the foregoing embodiment of the disclosure. Moreover, the constituent elements described in the foregoing embodiment of the disclosure may also be suitably combined.

Furthermore, according to the embodiment of the disclosure, a light source device is provided in the processor but may also be formed separately.

Moreover, although the embodiment of the disclosure is an endoscope system, same could also be applied, for example, to a capsule-type endoscope, a video microscope for imaging a subject, a mobile phone with an imaging function, and a tablet-type terminal with an imaging function.

In addition, although the embodiment of the disclosure is an endoscope system that includes a medical endoscope, same could also be applied to an endoscope system that includes an industrial endoscope.

Furthermore, in the embodiment of the disclosure, the foregoing "units" may also be replaced with "means" or "circuits". For example, "control unit" may be replaced with "control means" or "control circuit".

In addition, a program that is executed in the embodiment of the disclosure is file data that is in an installable format or an executable format and that is provided by being recorded on a recording medium that is computer-readable, such as a CD-ROM, a flexible disk (FD), a CD-R, a digital versatile disk (DVD), a USB medium, or a flash memory.

Furthermore, a program that is executed in the embodiment of the disclosure may be configured to be stored on a computer connected to a network such as the internet or to be provided by being downloaded over the internet. Furthermore, a program that is executed in the embodiment of the disclosure may be configured to be provided or distributed over a network such as the internet.

Note that, although expressions such as "first", "thereafter", and "next" are used in the flowchart descriptions in the present specification to illustrate the pre- and post-processing relationships between steps, the sequence of the processing required to carry out the disclosure is not necessarily uniquely defined by such expressions. In other words, the sequence of the processing in the flowcharts disclosed in the present specification may be revised within a consistent scope. Furthermore, the disclosure is not limited to or by a program including simple branch processing and determinations may be made by branching using a greater number of determination items overall. In such cases, a user may be encouraged to perform a manual operation, which may be combined with artificial intelligence technology for machine learning after learning is repeated. Moreover, by learning the operating patterns implemented by multiple experts, deep learning may be executed by introducing more complex conditions.

The disclosure affords the advantageous effect of enabling both efficiency and information security to be taken into account.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An endoscope system comprising:
a processor configured to perform image processing on endoscope image data acquired by an endoscope, which is inserted in a subject and observes an inside of the subject; and
a terminal device communicating with the processor, the terminal device including:
a transceiver configured to transmit identification information identifying the terminal device to the processor and receive, from the processor, processor identification information identifying the processor, and
a controller configured to:
determine whether the processor is a connection destination configured to perform two-way communication, based on the received processor identification information,
authenticate whether a user of the terminal device is a predetermined registered user by analyzing data obtained by the terminal device from the user, and
allow two-way communication between the processor and the terminal device in response to the processor being determined as the connection designation to perform two-way communication and in response to authenticating the user of the terminal device.

2. The endoscope system according to claim 1, wherein the two-way communication is wireless two-way communication.

3. The endoscope system according to claim 2, wherein:
the processor and the terminal device are configured to connect to a network, and
the controller of the terminal device is configured to allow wireless two-way communication between the processor and the terminal device, or wireless two-way communication between the network and the terminal device based on the processor being determined as the connection designation to perform two-way communication and based on authenticating the user of the terminal device.

4. The endoscope system according to claim 3, wherein, when the processor and the terminal device perform wireless two-way communication, the controller is configured to acquire, via the transceiver, at least one of a software program and setting information from the processor or from a server connected to the network, the software program being a computer-executable program of the endoscope system, and the setting information is information of respective devices constituting the endoscope system, which is set by the registered user.

5. The endoscope system according to claim 3, wherein:
the terminal device further includes a display configured to display images; and
the controller of the terminal device is configured to:
control display states of the display,
acquire the endoscope image data that is recorded in the processor or in a memory that is connected to the processor, and acquire, via the network, case image data stored on a server, and
cause the display to display an endoscope image corresponding to the endoscope image data and a case image corresponding to the case image data so as to enable a comparison of the endoscope image and the case image.

6. The endoscope system according to claim 3, wherein:
the terminal device further includes a memory configured to store information; and the controller is configured to:
control the memory,
acquire the endoscope image data, patient information relating to a patient who is the subject, and schedule information of the registered user, respectively, from the processor or from a server via the network, the schedule information including at least a patient rounds time period for performing rounds of the patient, and
store in the memory the patient rounds time period in association with the endoscope image data.

7. The endoscope system according to claim 3, wherein the controller is configured to perform authentication by acquiring any one or more of a facial image of the user, biological information of the user, and gesture information of the user.

8. The endoscope system according to claim 3, wherein:
the terminal device further includes an operating device which, in a state of the wireless two-way communication, is configured to receive an input of a resolution setting request signal setting a resolution of image data to be acquired for the processor or a server connected to the network, and
the controller is configured to cause the transceiver to transmit the resolution setting request signal to the processor or the server.

9. The endoscope system according to claim 3, wherein:
the terminal device further includes an imaging sensor configured to generate image data, and
the controller is configured to activate an imaging function of the imaging sensor by the user when the user has been authenticated as being the registered user.

10. The endoscope system according to claim 3, wherein:
the transceiver is configured to transmit information to outside an operating room, and
the controller is configured to allow transmission of the information to outside the operating room by the transceiver when the user has been authenticated as being the registered user.

11. The endoscope system according to claim 3, further comprising:
an operating device configured to receive an input of information,
wherein the controller is configured to cause the transceiver to transmit the inputted information from the operating device to a server connected to the network when the user has been authenticated as being the registered user.

12. The endoscope system according to claim 3, further comprising:
a wireless device connected to the network and configured to perform wireless two-way communication with the terminal device and the processor,
wherein, when the identification information has been received from the terminal device, the wireless device is configured to transmit, to the terminal device, connectivity determination information indicating whether the wireless device is configured to perform wireless two-way communication with the terminal device.

13. The endoscope system according to claim 12, wherein the terminal device or the wireless device is configured to hold the connectivity determination information and establish an automatic connection between the terminal device and the wireless device based on the connectivity determination information after the terminal device is powered on.

14. The endoscope system according to claim 3, wherein the controller is configured to transmit an indication that wireless two-way communication between the processor and the terminal device or wireless two-way communication between the network and the terminal device has been enabled.

15. The endoscope system according to claim 3, wherein:
the terminal device further includes a display configured to display images; and
the controller is configured to:
control display states of the display,
acquire, via the network from a server connected to the network, the endoscope image data which the processor transmitted to the server and case image data stored on the server, and
cause the display to display an endoscope image corresponding to the endoscope image data and a case image corresponding to the case image data so as to enable a comparison of the endoscope image and the case image.

16. The endoscope system according to claim 3, wherein:
the processor further includes a replacement device information recording unit configured to record device information relating to replaceable devices that is provided in the processor, the replacement device information recording unit being configured to wirelessly transmit the device information within a predetermined range, and
the controller is configured to acquire the device information from the replacement device information recording unit.

17. The endoscope system according to claim 16, wherein the controller is configured to transmit the device information acquired by the replacement device information acquisition unit to the server connected to the network.

18. A terminal device configured to communicate with a processor that performs image processing on endoscope image data acquired by an endoscope that observes an inside of a subject, the terminal device comprising:
a transceiver configured to transmit identification information identifying the terminal device to the processor and receive, from the processor, authentication information allowing two-way communication; and
a controller communicating with the transceiver, the controller being configured to:
determine whether the processor is a connection destination configured to perform two-way communication, based on the received processor identification information,
authenticate whether a user of the terminal device is a predetermined registered user by analyzing data obtained by the terminal device from the user, and
allow two-way communication between the processor and the terminal device in response to the processor being determined as the connection designation to perform two-way communication and in response to authenticating the user of the terminal device.

19. The terminal device according to claim 18, wherein the two-way communication is wireless two-way communication.

20. The terminal device according to claim 19, wherein:
the processor and the terminal device are configured to connect to a network, and
the controller is configured to allow wireless two-way communication between the processor and the terminal device, or wireless two-way communication between the network and the terminal device based on the processor being determined as the connection designation to perform two-way communication and based on authenticating the user of the terminal device.

21. A control method executed by an endoscope system including (i) a processor configured to perform image processing on endoscope image data acquired by an endoscope, which is inserted in a subject and observes an inside of the subject, the processor being configured to connect to a network, and (ii) a terminal device configured to communicate wirelessly with the processor or the network, the control method comprising:

transmitting identification information identifying the terminal device to the processor;

receiving, from the processor, authentication information allowing wireless two-way communication;

determining, based on the authentication information, whether the processor is a connection destination configured to perform wireless two-way communication;

authenticating whether a user of the terminal device is a predetermined registered user by analyzing data obtained by the terminal device from the user; and allowing wireless two-way communication between the processor and the terminal device, or wireless two-way communication between the network and the terminal device in response to the processor being determined as the connection designation to perform two-way communication and in response to authenticating the user of the terminal device.

* * * * *